US010114926B2

(12) United States Patent
Iwase et al.

(10) Patent No.: US 10,114,926 B2
(45) Date of Patent: *Oct. 30, 2018

(54) WORKFLOW TEMPLATE MANAGEMENT FOR MEDICAL IMAGE DATA PROCESSING

(71) Applicant: TeraRecon, Inc., Foster City, CA (US)

(72) Inventors: Akio Iwase, Brisbane, CA (US); Motoaki Saito, Tokyo (JP); Robert J. Taylor, San Francisco, CA (US); Tiecheng Zhao, Concord, MA (US); Vikram Simha, Boston, MA (US)

(73) Assignee: TERARECON, INC., San Mateo, CA (US)

(*) Notice: Subject to any disclaimer, the term of this patent is extended or adjusted under 35 U.S.C. 154(b) by 148 days.

This patent is subject to a terminal disclaimer.

(21) Appl. No.: 14/485,375

(22) Filed: Sep. 12, 2014

(65) Prior Publication Data
US 2015/0006203 A1 Jan. 1, 2015

Related U.S. Application Data

(63) Continuation of application No. 13/734,245, filed on Jan. 4, 2013, now Pat. No. 8,868,490, which is a
(Continued)

(51) Int. Cl.
*G06F 17/30* (2006.01)
*G06F 19/00* (2018.01)
(Continued)

(52) U.S. Cl.
CPC ............ *G06F 19/321* (2013.01); *G06F 17/30* (2013.01); *G06F 17/3028* (2013.01);
(Continued)

(58) Field of Classification Search
None
See application file for complete search history.

(56) References Cited

U.S. PATENT DOCUMENTS 6,570,578 B1 5/2003 Smirnov et al.
6,904,161 B1 6/2005 Becker et al.
(Continued)

FOREIGN PATENT DOCUMENTS

JP 2003-523801 8/2003
JP 2003-271924 9/2003
(Continued)

OTHER PUBLICATIONS

European Patent Application No. 09808903.0, Extended European Search Report, 7 pages.
(Continued)

*Primary Examiner* — Amresh Singh
(74) *Attorney, Agent, or Firm* — Womble Bond Dickinson LLP

(57) ABSTRACT

According to one embodiment, workflow templates are maintained, each workflow template including a predefined sequence of workflow stages associated with a particular type of medical diagnosis or process. In response to a request for processing medical image data from a user, a user identifier (ID) that identifies the user is automatically determined based on the request. At least one of the workflow templates that is specifically configured to process medical image data associated with the user is identified based on the user ID. One or more image processing operations defined by the identified workflow template are performed on the medical image data, generating a scene corresponding to an image view representing the medical image data. The scene associated with each of the workflow stages is stored in a persistent storage, where a scene includes metadata used to recreate a corresponding medical image view subsequently.

24 Claims, 9 Drawing Sheets

Related U.S. Application Data continuation of application No. 12/196,099, filed on Aug. 21, 2008, now Pat. No. 8,370,293.

(51) Int. Cl.
    *G06Q 10/06*         (2012.01)
    *G06Q 50/22*         (2018.01)

(52) U.S. Cl.
    CPC ....... *G06F 17/30312* (2013.01); *G06Q 10/06* (2013.01); *G06Q 10/0633* (2013.01); *G06Q 50/22* (2013.01)

(56) References Cited

U.S. PATENT DOCUMENTS

| | | | |
|---|---|---|---|
| 7,264,000 | B2 | 9/2007 | Paolitto et al. |
| 8,117,549 | B2 * | 2/2012 | Reiner ................. G06F 19/321 600/407 |
| 2004/0139222 | A1 | 7/2004 | Silk et al. |
| 2004/0254465 | A1 | 12/2004 | Sano et al. |
| 2006/0239589 | A1 * | 10/2006 | Omernick ............. G06F 19/321 382/293 |
| 2006/0285730 | A1 | 12/2006 | Habets et al. |
| 2008/0130824 | A1 | 6/2008 | Fujisawa |
| 2012/0014559 | A1 | 1/2012 | Suehling et al. |

FOREIGN PATENT DOCUMENTS

| | | |
|---|---|---|
| JP | 2006-094956 | 4/2006 |
| JP | 2006-305371 | 11/2006 |
| JP | 2008-161675 | 7/2008 |
| WO | WO 01/54066 | 7/2001 |
| WO | WO 02/39899 A2 | 5/2002 |
| WO | WO 03/043501 | 5/2003 |
| WO | WO 2007/050962 A2 | 5/2007 |
| WO | WO 2007/059020 | 5/2007 |

OTHER PUBLICATIONS

Office Action dated Aug. 7, 2013 for corresponding Japanese Patent Application No. 2011-524057, 4 pages.
International Search Report and Written Opinion dated Oct. 2, 2009, for International Application No. PCT/US2009/054694, filed Aug. 21, 2009, 10 pages.

* cited by examiner

FIG. 4

WORKFLOW TEMPLATE MANAGEMENT FOR MEDICAL IMAGE DATA PROCESSING

RELATED APPLICATIONS

This application is a continuation of co-pending U.S. patent application Ser. No. 13/734,245, filed Jan. 3, 2013, which is a continuation of U.S. patent application Ser. No. 12/196,099, filed Aug. 21, 2008, now U.S. Pat. No. 8,370,293. The disclosure of the above applications is incorporated by reference herein in its entirety.

TECHNICAL FIELD

This invention is related to using workflow templates to manage and process medical image data generated from medical imaging devices.

BACKGROUND

Medical image data, which are collected with medical imaging devices, such as X-ray devices, Magnetic Resonance Imaging (MRI) devices, Ultrasound devices, Positron Emission Tomography (PET) devices or Computed Tomography (CT) devices in the diagnostic imaging departments of medical institutions, are used for an image interpretation process called "reading" or "diagnostic reading." After an image interpretation report is generated from the medical image data, the image interpretation report, possibly accompanied by representative images or representations of the examination, are sent to the requesting physicians. Today, these image interpretation reports are usually digitized, stored, managed and distributed in a Radiology Information System (RIS) with accompanying representative images and the original examination stored in a Picture Archiving Communication System (PACS) which is often integrated with the RIS.

Recent developments in multi-detector computed tomography (MDCT) scanners and other scanning modalities provide higher spatial and temporal resolutions than the previous-generation scanners. However, the drawback to the superior image detail and information from the MDCT scanners is the volume of datasets acquired by these scanners, especially during CT angiographic procedures. For example, in certain multi-phase acquisitions, a CT examination can generate over 6000 images with the latest scanners. Accordingly, the data sets can reach a size of several gigabytes, while the acquisition times are only measured in seconds.

Under some traditional approaches, when a physician orders an examination, the patient is scanned by the medical imaging device to collect medical image data related to certain part of the body. Afterwards, the collected medical image data is transferred to stand-alone advanced processing workstations, or to distributed software applications with similar functionality, which include a suite of post-processing tools. A technologist who has access to a workstation generates some limited static images based on the medical image data, and provides the images to the interpreting physician who may use them to support the diagnostic interpretation process, and potentially include them with the image interpretation report given to the ordering physician. Because of the limitation of this processing pipeline, often less than 5% of the data contained in the original dataset is received by the ordering physician. Also, it takes longer for the physician to perform his duty while waiting for the technologist to finish the processing. As a result, since workload and time has to be prioritized based, non-optimal diagnosis may occur, and non-optimal surgery might be performed.

A more sophisticated facility would utilize a Picture Archiving and Communication System (PACS) to store original medical image data, and distribute the data to PACS viewing stations for generating reports. Still, even with the help of PACS, workflow for processing medical image data remains under a similar approach. Once the original image data has been acquired, it is usually transferred to different medical personnel or departments for diagnostic review. Various levels of technologists process and generate intermediate images before distributing them to the ordering physicians for further review. Also, these diagnostic reviews can only be performed on a limited number of isolated PACS viewing stations or stand-alone workstations.

Even with the better technologies, when intermediate images are generated, valuable information are still either filtered out, or failed to be included, from the original image dataset. The end report may contain only a fraction of the original data, limiting the ordering physician's ability to fully take advantage of the examination that has been performed. Also, restricted access to the original image dataset hinders the ordering physician ability to perform the image processing or image review himself or herself, and hence the ordering physician is forced to rely upon the perspective of the interpreting physician, even though that perspective (one of diagnosis) may be quite different from the perspective of the ordering physician (who is then responsible for devising and implementing a therapeutic plan).

Today, it has become possible to render three-dimensional (3D) images using multiple sets of tomographic data captured from different cross-sectional positions. For 3D image processing, it is not possible to store in advance all the possible spontaneous views a physician might utilize. A complete set of original image data has to be present on a 3D processing system which can generate arbitrary 3D views in real time and on demand. Therefore, with an explosion of data volume acquired from MDCT and other scanners, transporting complete datasets across the network to various workstations puts a prohibitive burden on a facility's IT infrastructure.

BRIEF DESCRIPTION OF THE DRAWINGS

The present invention is illustrated by way of example and not limitation in the figures of the accompanying drawings, in which like references indicate similar elements and in which:

FIG. 4 illustrates an exemplary Workflow Management System user interface, in accordance with one embodiment of the present invention;

DETAILED DESCRIPTION

Figure 1:
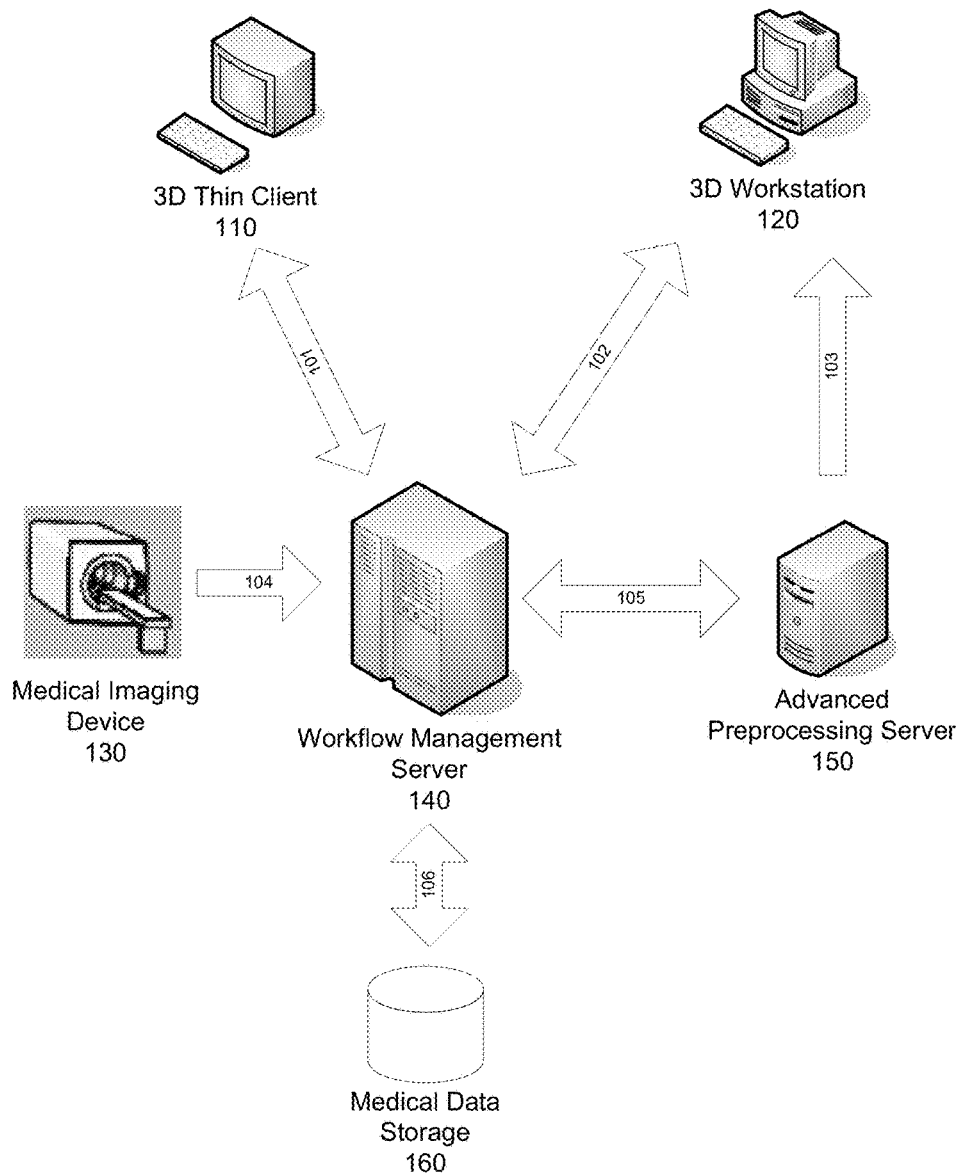
FIG. 1 illustrates an exemplary configuration of a Workflow Management System environment in accordance with one embodiment of the present invention.

Described herein are embodiments of methods and apparatuses for a workflow management system to process medical image data generated by medical imaging devices. In one embodiment, medical imaging devices create images of human body parts for clinical purposes, by utilizing modern imaging techniques such as X-ray, CT, ultrasound, Magnetic Resonance Imaging (MRI), or nuclear medicine, etc. As used herein, medical image data refers to raw image outputs generated by medical imaging devices, and can be stored in Digital Imaging and Communications In Medicine (DICOM) format. Medical image data may be further analyzed and processed to generate medical image views for medical diagnosis.

In one embodiment, a workflow is defined to capture the repetitive pattern of activities in the process of medical diagnosis, such as various image generation operations. A workflow arranges these activities into a process flow according to various factors, such as each activity's order, functions, resources requirements, and outputs, etc. Each activity in a workflow is called a workflow stage. Thus, a workflow stage, also referred to as a workflow element, captures various details of an activity, such as the activity's function, inputs received, and outputs generated, etc.

In one embodiment, a workflow template is created for a specific type of medical diagnosis or processing. A workflow template is a template with a predefined set of workflow stages. Each workflow stage in the workflow template includes one or more image processing operations. These image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved.

In another embodiment, a user selects one previously created workflow template and applies it to a set of medical image data for a specific medical study. Alternatively, a default workflow template may be provided to the user automatically based on the macro anatomy of the medical image data and/or the identity of the user. For example, a particular user (e.g., a radiologist) may set a certain predefined cardiac workflow template as the user's default workflow template for cardiac scans. The application of the workflow template to the medical image data creates a workflow scene. A workflow scene is an entity for tracking the progression of, and for recording the results of, processing through a workflow. Once created, the workflow scene contains the same workflow stages as defined in the workflow template it is created from. A user can follow the workflow logic as defined in the workflow scene, and proceed to a next workflow stage after finishing one, without the presence of the workflow template. Thus, for any given workflow scene, the user can quickly grasp its current processing status and its remaining workflow stages that need to be performed.

A workflow scene also contains a collection of scenes for storing results generated from the processed workflow stages. A scene contains metadata generated from one workflow stage. The metadata in the scene is generated by the image processing operations of the workflow stage, when applying to the medical image data to produce a set of medical image views. Once a workflow stage is completed, the resulted scene can be added into the collection of scenes in the workflow scene. Thus, the collection of scenes provides a history of what have been performed in one workflow scene.

In one embodiment, a scene can be applied to the medical image data to reproduce the set of medical image views. When reviewing the medical image views reproduced from a scene, a user may adjust these image views by making updates to the image processing parameters (metadata) contained in the scene. Afterwards, the updated image processing parameters can be saved to the scene to replace the previously stored image processing parameters. The newly updated scene can also be stored in the workflow scene to replace the old scene. Alternatively, a new series of workflow scene can be independently maintained to store one route of processing the medical image data through the workflow.

In some embodiments, a workflow template may be user-created for processing a specific type of medical image data. The user could add either predefined workflow stages, or customized workflow stages, to the workflow template. When processing a sample medical image data, the manual adjustments and configurations during the processing can be recorded and stored as image processing operations into a customized workflow stage. The customized workflow stage can then be applied to other medical image data to perform the same image processing operations as recorded during the workflow stage creation.

In some embodiments, a workflow scene is automatically generated by a preprocessor based on a workflow template. Since a workflow template contains predefined workflow stages with information on how to process, and the order of processing, medical image data, the preprocessor could utilize the workflow template to start the automated processing as soon as the medical image data is collected and made available. Alternatively, the preprocessor could automatically generate scenes for a workflow scene. A user may accept, or make minor updates to the auto-generated scenes when reviewing the workflow scene.

FIG. 1 illustrates a system diagram showing a configuration of image diagnosis device and various processing systems, in accordance with one embodiment of the present invention. In one embodiment, devices 110-160 are interconnected in a network environment. The network environment is implemented by physical connections, wireless communications, or a combination of the above. Data and network messages are transported among devices 110-160 via communication channels 101-106.

In some embodiments, Medical Imaging Device 130 is an image diagnosis device, such as X-ray CT device, MRI scanning device, Nuclear Medicine device, Ultrasound device, or any other medical imaging device. It collects information from multiple cross-section views of a specimen, reconstructs them, and produces medical image data for the multiple cross-section views. In one embodiment, the collected medical image data are in DICOM format. After collection, the medical image data are transferred to Workflow Management Server 140 via communication channel 104, and saved in Medical Data Storage 160 by the Workflow Management Server 140 through storage connection 106. Medical Imaging Device 130 is also referred to as a modality.

Workflow Management Server 140 performs multiple functions according to some embodiments of present invention. It performs a data server function in acquiring and storing medical image data received from Medical Image Device 130. It also acts as a graphic engine in processing the medical image data to generate 2D or 3D medical image views. In one embodiment, a client/server Workflow Management System is installed on the Workflow Management Server 140. The Workflow Management System includes client partition and server partition. The server partition of the Workflow Management System runs on the Workflow Management Server 140, and communicates with its client partition installed on 3D Thin Client 110 or 3D Workstation 120 via communication channels 101 and 102, respectively. In one embodiment, the Workflow Management System is distributed and running on multiple workflow management servers. In another embodiment, the Workflow Management System is a web-enabled application operating on a Workflow Management Server 140. Any computer with web-browsing application installed may access and utilize the Workflow Management System without any additional hardware and/or software requirements.

In one embodiment, the Workflow Management Server 140 is a data server for medical image data received from Medical Imaging Device 130 via communication channel 104. The received medical image data is then stored into Medical Data Storage 160 via communication channel 106. In one embodiment, when 3D Workstation 120 requests for unprocessed medical image data via communication channel 102, the Workflow Management Server 140 retrieves the data from the Medical Data Storage 160, and serves the retrieved data as stored to 3D Workstation 120 via communication channel 102.

In one embodiment, the Workflow Management Server 140 includes a graphic engine capable of performing 2D and 3D images generating. When 3D Thin Client 110 or 3D Workstation 120 requests for certain medical image views, the Workflow Management Server 140 retrieves medical image data stored in Medical Data Storage 160, and renders 2D or 3D medical images views from the medical image data. The end results for medical image views are sent to 3D Thin Client 110 via communication channel 101, or 3D Workstation 120 via communication 102.

In one embodiment, when a user making adjustments to the medical image views received from the Workflow Management Server 140, these user adjustment requests are sent back to the Workflow Management Server 140. The Workflow Management Server 140 then performs additional graphic processing based on the user requests, and the newly generated, updated medical image views are returned to 3D Thin Client 110 or 3D Workstation 120. This approach is advantageous because it eliminates the need to transport large quantity of unprocessed medical image data across network, while providing 2D or 3D image viewing to client computers with no 2D or 3D image processing capacity.

In one embodiment, the Workflow Management Server 140 includes a Workflow Management System. The Workflow Management System can be implemented as a stand-alone application, a client/server application, or a web-enabled application, etc. When implemented as a standalone application, all functionalities of the Workflow Management System reside in one computer system, e.g., a Workflow Management Server 140. A user may access the Workflow Management System locally from the computer system, or remotely via a mechanism to remote control (e.g., Remote Desktop Connection, Virtual Network Computing, etc) the computer system.

In another embodiment, when implemented as a client/server application, the Workflow Management System includes a client-side partition and a server-side partition. Functionalities of the Workflow Management System are distributed to the client-side or server-side partitions. When a substantial amount of functionalities are distributed to the client-side partition, the Workflow Management System may be referred to as a "thick client" application. Alternatively, when a limited amount of functionalities are distributed to the client-side partition, while the majority of functionalities are performed by the server-side partition, the Workflow Management System may be referred to as a "thin client" application. In another embodiment, functionalities of the Workflow Management System may be redundantly distributed both in client-side and server-side partitions.

In one embodiment, the Workflow Management System is implemented as a web-enabled application. Any computer with web-browsing software installed may function as a client of, and communicate with, the Workflow Management System via a web server (not shown in FIG. 1). The web server may be a third-party web server (e.g., Apache® HTTP Server, Microsoft® Internet Information Server, etc), or an embedded component of the Workflow Management System. The web server routes HTTP requests and responses between the client and the Workflow Management System, allowing the client to access all functionalities implemented in the Workflow Management System.

In one embodiment, the server-side partition of the Workflow Management System receives requests from multiple client-side partitions of the Workflow Management System, processes the requests, and returns results back to the respective requesting client-side partitions. In one embodiment, the client-side partition is installed on 3D Thin Client 110, 3D Workstation 120, PACS, or any computer systems intending to access the Workflow Management System. In this case, the functions of Workflow Management System may be performed on 3D Thin Client 110, 3D Workstation 102, Workflow Management Server 140, PACS, or the combination of the above.

In one embodiment, the Workflow Management System manages the creation, update and deletion of workflow templates. It also performs workflow scene creation when receiving user requests to apply a workflow template to medical image data. After a user validates the results generated from processing a workflow stage predefined in the workflow template, the Workflow Management System creates a new scene and stores the new scene to the workflow scene. The Workflow Management System also allows the updating and saving of scenes during user adjustments of the medical image views generated from the scenes.

In one embodiment, Medical Data Storage 160 serves as data storage for DICOM and/or other data objects. The Workflow Management Server 140 utilizes the Medical Data Storage 160 to store and retrieve medical image data, workflow templates, workflow scenes, and other data. In another embodiment, the Medical Data Storage 160 provides redundant storage for thin slice DICOM data obtained from external DICOM compatible devices not shown in FIG. 1. The Medical Data Storage 160 may be implemented as internal storage of Workflow Management Server 140. It may also be implemented with one or more Storage Servers in a Storage Area Network (SAN) environment, a Network-attached Storage (NAS) environment, or a combination thereof. Further, the Medical Data Storage 160 may be implemented in multiple redundant storage devices or multiple Database Management Systems (DBMS).

In one embodiment, Medical Data Storage 160 is implemented with Relational Database Management Systems (RDBMS), e.g., Oracle® Database or Microsoft® SQL Server, etc. A Unique Identifier (UID) field of the DICOM data stored in Medical Data Storage 160 is indexed for fast retrieval of the DICOM data. Indexing utilizes special data storage structures, such as hash tables, to quickly find data based on a unique key of the data. Indexing also enables the DBMS systems to improve data retrieval by using caching and other optimizing mechanisms.

In one embodiment, 3D Thin Clients 110 is a desktop computer with network access to the Workflow Management Server 140. Alternatively, 3D Thin Client 110 may be a PACS or any computer systems having client-side partition of the Workflow Management System installed, with or without 3D processing capacity. When processing non-3D medical image views, no specific 3D software is required on the client computers. Therefore, 3D Thin Client 110 does not necessarily have 3D image processing capability, and may not be implemented with a "thin client" application. Alternatively, 3D Thin Client 110 may be implemented on a more powerful computing machine, such as a PACS.

In one embodiment, Thin-client 3D software is installed on 3D Thin Client 110, allowing it to communicate with the graphic engine operating on the Workflow Management Server 140. By taking advantage of the processing power of the Workflow Management Server 140, 3D Thin Client 110 may perform similar functions as a 3D workstation 120 to view, manipulate and store 3D images. When viewing and updating 3D medical image views on a 3D Thin Client 110, the medical image data that the image views are originated from is not uploaded to the 3D Thin Client 110. Instead, the Workflow Management Server 140 performs graphic processing of the medical image data. And only the end results in medical image views are sent from the Workflow Management Server 140 and received by the 3D Thin Client 110. This configuration allows flexibility in setting up any computer as a 3D Thin Client 110, without burdening a medical facility's network throughput.

In another embodiment, the 3D Thin Client 110 is configured with client-side partition of the Workflow Management System to communicate with the server-side partition of the Workflow Management System on the Workflow Management Server 140. The client-side partition receives various user requests and forward these requests to the Workflow Management Server 140 via communication channel 101. The server-side partition processes the user requests and returns responses back to the 3D Thin Client 110. The 3D Thin Client 110 then performs additional functions based on the return responses, and displays information to the user. In another embodiment, the client-side partition may include tools and functions to perform adjustment and configuration to the Workflow Management System.

In one embodiment, 3D Workstation 120 is a stand-alone computer with hardware (e.g, graphics cards, memory, hard-drive, fast network, etc.) supports to perform 3D image rendering. 3D Workstation 120 is also installed with visualization software and tools for advanced editing and processing of medical images. In one embodiment, medical image data for a particular diagnosis study is transported from the Workflow Management Server 140 to a 3D Workstation 120 via communication channel 102. Once received, the 3D Workstation 120 is capable of generate 3D images independently, without relying on the graphic engine of the Workflow Management Server 140. In another embodiment, the 3D Workstation 120 is optional, since the Workflow Management Server 140 has the capacity in performing the same 3D image rendering. In a further embodiment, 3D Workstation 120 is installed with the client-side partition of the Workflow Management System, allowing it to perform similar functions as a 3D Thin Client 110 in interacting with the Workflow Management Server 140.

In one embodiment, Advanced Preprocessing Server 150 performs automated pre-processing of medical image data managed by the Workflow Management Server 140. Based on embedded information in DICOM objects and other user configurations, the Advanced Preprocessing Server 150 automatically processes newly acquired medical image data offline, without the Workflow Management Server 140's involvement. Upon completion, the results of the rendering are automatically sent to the Workflow Management Server 140 for storing in the Medical Data Storage 160. In another embodiment, the automatically pre-processed results are also sent to 3D Workstation 120, allowing a specialist on the 3D Workstation 120 to perform quality assurance on the automatic pre-processing.

In another embodiment, a DICOM object's detail information, such as the type of study or equipment used to collect the medical image data, are obtained. Based on this information, the Advanced Preprocessing Server 150 identifies the typical processing operations for the type of DICOM data generated from the specific equipment, and pre-processes these operations against the medical image data embedded in the DICOM object. In another embodiment, the Advanced Preprocessing Server 150 obtains workflow scene data. And based on the embedded workflow stages information, the Advanced Preprocessing Server 150 automatically pre-processes the medical image data through every workflow stage within the workflow scene, before a user starting to work on the medical image data. This approach provides an automated Workflow Management System.

In another embodiment, the results generated by the Advanced Preprocessing Server 150 pre-processing include a collection of scenes. Each scene can be quickly loaded by the Workflow Management System when a user prepares to process a workflow stage in a workflow scene. After loading, the preprocessing generated scene functions the same as a manually generated scene from the workflow stage. This approach is advantageous because the pre-processing is performed on the Advanced Preprocessing Server 150, thus freely up resources on the Workflow Management Server 140. Also, the pre-processing provides a quicker response time for user accessing the Workflow Management System functionalities.

Figure 2:
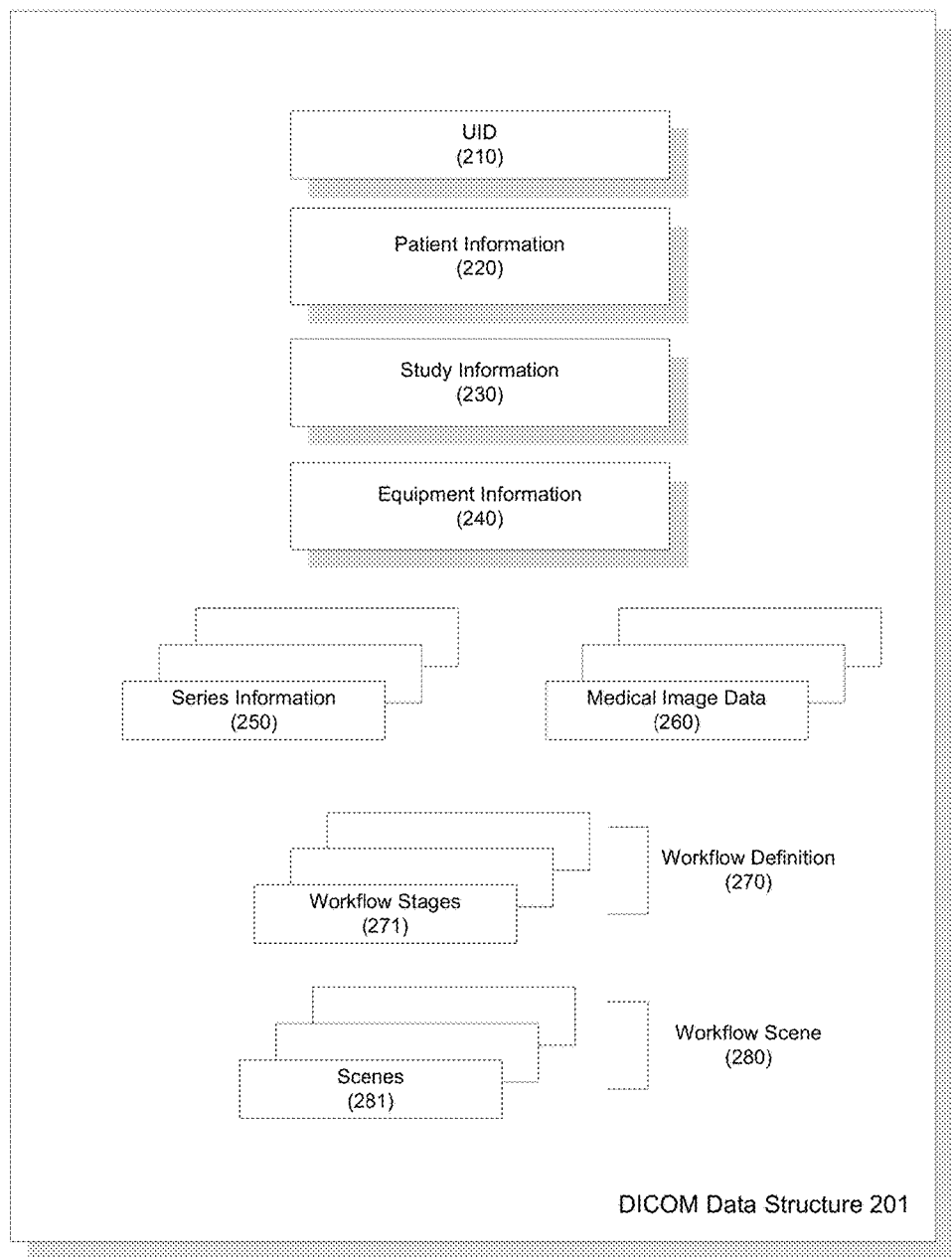
FIG. 2 illustrates an exemplary DICOM data structure for the Workflow Management System in accordance with one embodiment of the present invention.

FIG. 2 illustrates a DICOM Data Structure 201, in accordance with one embodiment of the present invention. DICOM is a standard for storing, processing, and transmitting medical imaging information. It is developed by the DICOM Standards Committee and is maintained by the National Electrical Manufacturers Association (NEMA). DICOM standards allow integrations of medical scanners, servers, and workstations in a PACS environment. DICOM standard defines multiple datasets, each of which serves a specific function. Alternatively, embodiments of the present invention may be implemented in proprietary data structure, without using DICOM standard.

In FIG. 2, Data Structure 201 is an example of a DICOM object containing multiple datasets that can be utilized in storing medical image data as well as workflow related data structures. All of the datasets in Data Structure 201 may or may not be present at the same time. Data Structure 201 may contain additional datasets not present in FIG. 2. And a DICOM object in Data Structure 201 format may be stored in one single file or be split into multiple files, depending on the storage and transportation needs.

In one embodiment, Section 210 is an UID (Unique Identifier) for the DICOM Data Structure 201. The UID may be implemented using Universally Unique Identifier (UUID), Global Unique Identifier (GUID), or other unique identifiers. Since UUID or GUID allows distributed systems to maintain uniqueness without using a centralized coordination, utilizing such identifier enables distributing and interchanging of DICOM objects with external software and systems without the concern of duplicated UID. An UID allows quick search and retrieval of data from Medical Data Storage 160 of FIG. 1. It may be automatically generated by the Workflow Management System, with or without user interaction.

Referring back to FIG. 2, in one embodiment, Section 220 is a dataset of Patient Information associated with the medical images. The Patient Information contains a patient's biographic information as well as uniquely assigned patient ID. Since the patient ID is stored within the DICOM file, the image data stored in the DICOM file may not be separated from the Patient Information. Also, a unique patient ID allows fast search and easy retrieval of the datasets. Section 230 of FIG. 2 is a dataset for Study Information. In one embodiment, Study information contains details of the medical examination or diagnosis for one specific patient, such as the date and time of the study performed, the ordering physician or referring physician information, etc.

Section 240 of FIG. 2 is a dataset for Equipment Information. In one embodiment, Equipment Information contains detail of Medical Imaging Device 130, as described in FIG. 1, used to generate the image data. Section 250 of FIG. 2 describes a collection of Series Information datasets. In one embodiment, a set of medical image data may go through multiple series of processing, each series performing a different aspect of manipulation. One Series Information 250 dataset captures the detail information for one series of processing. In another embodiment, medical image data may go through multiple series of processing in parallel for the same workflow. Each series is an independent route of processing through each workflow stage of a workflow. This approach is advantageous because it allows a high degree of independence, enabling customized workflow progression. In one embodiment, medical image data collected from Medical Imagine Device 130 of FIG. 1 are treated as one series. Therefore, one Series Information 250 dataset is utilized to store information for the medical image data.

Referring back to FIG. 2, Section 260 contains multiple sets of medical image data. Each dataset in Section 260 stores one set of medical image data collected from Medical Imaging Device 130 of FIG. 1. In one embodiment, each Section 260 stores one slice of two-dimensional medical image data. In another embodiment, a slab (multiple slices) of medical image data is stored in one Section 260. Further, medical image views generated from medical image data may be stored in Section 260. Medical image data stored in Section 260 can be in its native, uncompressed format, or be in compressed format using various graphic compressing standards, such as JPEG, etc. In another embodiment, characteristics of the medical image data, such as size and depth of the image pixels, are also stored in Section 260.

Referring back to FIG. 2, Section 270 stores datasets related to a Workflow Definition. In one embodiment, Workflow template and its predefined workflow stages are stored in data structure not related to DICOM standard. It is advantageous to use other types of data structure, instead of DICOM objects, when implementation of the Workflow Management System requires simplified workflow template and workflow stage objects. When applying a workflow template to medical image data to generate a workflow scene, the workflow definition (e.g., the workflow stages predefined in the workflow template) are converted into Workflow Stages 271 in Section 270 of the DICOM Data Structure 201.

Section 280 of FIG. 2 stores dataset for a Workflow Scene with multiple Scenes 281. In one embodiment, a DICOM object containing Workflow Scene 280 may be utilized in performing Workflow Management. The Workflow Scene 280 may be identified and stored in a private tag in the DICOM object, without utilizing any predefined DICOM data sections. Workflow Stages 271 converted from a workflow template may also be stored and associated with the Workflow Scene 280 in the DICOM object. Also, a representative image, such as an image from the medical image data, or an image generated by metadata from one of the workflow stages, may also be stored and associated with the Workflow Scene 280 and/or Scenes 281. Alternatively, workflow template and its predefined workflow stages may be stored in DICOM object in a similar fashion. And Workflow Scene 280 and Scenes 281 may be implemented by data structure not related to DICOM standard.

Figure 3:
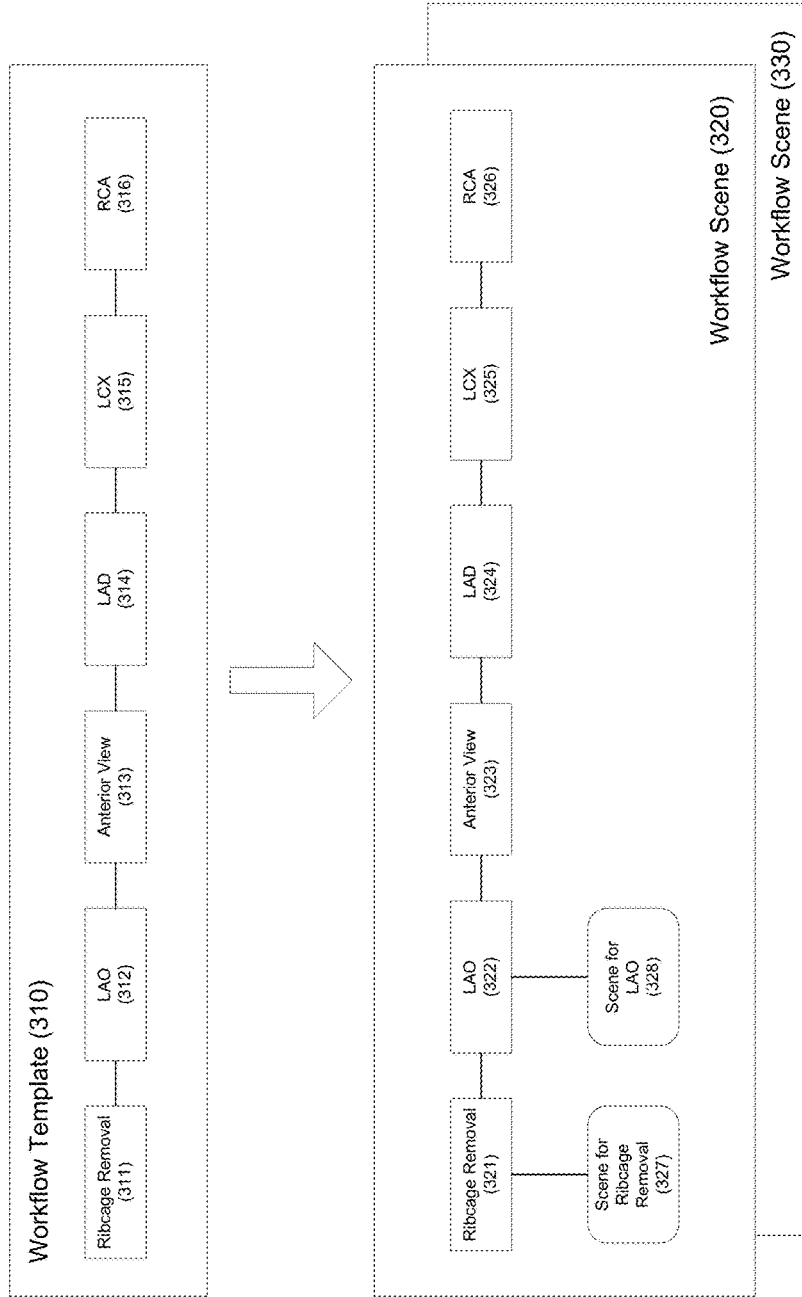
FIG. 3 illustrates an exemplary workflow template and workflow scenes for cardiac analysis, in accordance with one embodiment of the present invention.

FIG. 3 illustrates an exemplary Workflow Template 301 and multiple series of Workflow Scenes 320 and 330 for one specific cardiac diagnosis, in accordance with one embodiment of the present invention. In one embodiment, a workflow is defined to capture the repetitive pattern of activities in the process of generating medical image views for diagnosis. A workflow arranges these activities into a process flow according to the order of performing each activity. Each of the activities in the workflow has a clear definition of its functions, the resource required in performing the activity, and the inputs received and outputs generated by the activity. Each activity in a workflow is called a workflow stage, or a workflow element. With requirements and responsibilities clearly defined, a workflow stage of a workflow is designed to perform one specific task in the process of accomplishing the goal defined in the workflow. For many medical image studies, the patterns of activities to produce medical image views for diagnosis are usually repetitive and clearly defined. Therefore, it is advantageous to utilize workflows to model and document real life medical image processing practices, ensuring the image processing being properly performed under the defined procedural rules of the workflow.

In one embodiment, a workflow for a specific medical image study is modeled by a workflow template. A workflow template is a template with a predefined set of workflow stages forming a logical workflow. The order of processing an activity is modeled by the order established among the predefined set of workflow stages. In one embodiment, workflow stages in a workflow template are ordered sequentially, with lower order stages being performed before the higher order stages. In another embodiment, dependency relationships are maintained among the workflow stages. Under such arrangement, a workflow stage cannot be performed before the workflow stages it is depending on being performed first. In a further embodiment, advanced workflow management allows one workflow stage depending on multiple workflow stages, or multiple workflow stages depending on one workflow stage, etc.

In one embodiment, each workflow stage in a workflow template includes one or more image processing operations implementing the specific task assigned to the workflow stage. The image processing operations takes medical image data collected from Medical Imagine Device 130 of FIG. 1 as inputs. They perform specific processing on the medical image data and generate metadata as outputs. In another embodiment, a workflow stage takes metadata generated from a depended workflow stage as one of the inputs, and processes the medical image data with the help of the input metadata.

In one embodiment, metadata is data for describing, processing, and/or managing other data. Metadata generated by the image processing operations includes multiple image processing parameters. Each image processing operation produces one or more image processing parameters. In some embodiments, at least three types of image processing parameters are produced: image specific parameters, processing parameters, and displaying parameters. Image specific parameters describe identification, size and format of the medical image data processed. Processing parameters describe functions and algorithms related parameters utilized during processing. Displaying parameters, such as zooming, viewing projections, threshold, or highlighted area, are utilized in rendering result medical image views.

In one embodiment, metadata generated by workflow stages can be applied to medical image data to produce medical image views. Medical image views include viewable 2D or 3D graphic images that can be interactively adjusted or manipulated by a user. When processing medical image data through an image processing operation of one workflow stage, one or more medical image views are generated along with a set of image processing parameters, also referred to as metadata. A set of software tools is also provided to the user to adjust the image processing parameters. The adjustment of image processing parameters may update the medical image views displayed, allowing the user to fine tune the medical image views.

In one embodiment, the rendered medical image views are not permanently stored. Instead, the image processing parameters used to generate medical image views from medical image data may be converted into a DICOM format object, transported by Workflow Management System, and stored in Medical Data Storage 160 of FIG. 1. Such approach is advantageous since it allows quick and robust reproduction of the medical image views by applying the metadata to the original medical image data. Metadata also takes less storage and is easier to transport in comparison to medical image views. In another embodiment, the rendered medical image views are temporary cached in the memory of Workflow Management Server 140 or in Medical Data Storage 160 of FIG. 1. Caching the medical image views allows quick response time by eliminating the reproducing of the medical image views. Alternatively, the medical image views may be output directly to one or more reports, which may be delivered to one or more predetermined sites (e.g., radiologist's office, emergency room, intensive care unit, etc.). Furthermore, a particular site's report may actually drive the workflow template. In some embodiments, a workflow template may be used as a report generator to collect all relevant metadata from various workflow stages.

In one embodiment, Workflow Template 310 of FIG. 3 provides a workflow template with predefined set of workflow stages 311-316 for performing one specific cardiac diagnosis. Stage 311, the first stage in Workflow Template 310, performs 3D ribcage removal on medical image data to remove any image data related to a human ribcage. Based on the density information of the source image pixels, image processing operations of stage 311 remove pixels with high bone density, thereby exposing blood vessels and heart tissues underneath. After performing stage 311, generated metadata could be utilized to render medical image views with a clear view of the heart and coronary arteries. In the embodiment as illustrated in FIG. 3, stages 312-316 depend on stage 311's ribcage removal before performing their respective functions.

In one embodiment, a user selects the created Workflow Template 310 and applies it to a set of medical image data. The application of the Workflow Template 310 creates a Workflow Scene 320. A workflow scene is an entity for tracking the progression of, and for recording the results of, processing through a workflow. Once created, Workflow Scene 320 contains the same workflow stages 321-326 as defined in the Workflow Template 310, and is associated with the set of medical image data used during creation. Such approach is advantageous since it allows independent processing of Workflow Scene 320 without requiring the presence of the Workflow Template 310. Thus, in a workflow scene, a user could quickly grasp the workflow stages that need to be performed. In another embodiment, the newly created Workflow Scene 320 is associated with the Workflow Template 310 it was created from. Associating with a workflow template allows a workflow scene to utilize the workflow stages contained in the workflow template, instead of containing the same workflow stages. This approach is advantageous when the workflow does not require customization or user adjustments.

In one embodiment, a workflow scene may contain a collection of scenes for storing results generated from the processed workflow stages in the workflow scene. A scene contains metadata generated from one workflow stage. Once a workflow stage completes its processing, the result metadata can be stored in a scene, which is associated with the workflow stage. Afterwards, the scene is added into the collection of scenes in the workflow scene. Thus the collection of scenes provides user a history of what have been performed in a workflow, while the workflow stages without associated scenes show all the remaining tasks yet to be performed. Further, each scene may be utilized to recreate the historical stage in the workflow processing. Therefore, no information in medical image data is filtered out during workflow processing. A user may be able to recreate, evaluate, and/or reprocess each of the previously processed workflow stages by applying the scene associated with the workflow stage to medical image data. In some embodiments, an individual scene or a collection of scenes may be output directly to one or more reports.

In one embodiment, workflow stage 321 performs ribcage removal on the associated medical image data and generates metadata. The metadata can be saved in a Scene for Ribcage Removal 327. And Scene 327 is associated with Workflow Stage 321. Workflow stage 322 performs Left Anterior Oblique (LAO) processing of medical image data. Since stage 322 is a dependent on stage 321, metadata stored in scene 327 is utilized to generate intermit results from medical image data. Afterwards, image processing operations of stage 322 can be performed on these intermit results, and the resulted metadata can be stored in Scene for LAO 328. And scene 328 is associated with stage 322.

In one embodiment as illustrated in FIG. 3, stage 323 can be used to generate an Anterior View of a heart, stage 324 to generate a view of the Left Anterior Descending (LAD) artery (one of the coronary arteries of the heart), stage 325 to generate a view of the Left Circumflex Artery (LCX) (one of the coronary arteries of the heart), and stage 326 to generate a view of the Right Coronary Artery (RCA) (one of the coronary arteries of the heart). Since there are two scenes associated with stages 321 and 322, and there is no scene associated with stages 323-326, a user could review the history of workflow processing by evaluating scenes 327 and 328, or proceed to the next stage 323 of the workflow processing.

In one embodiment, a second series of Workflow Scene 330 is created from Workflow Template 310 based on the same set of medical image data that is previously associated with Workflow Scene 320. Workflow Scene 330 is independent from Workflow Scene 320 in workflow processing. It contains the same workflow stages as stages 321-326. However, it may contain different scenes, which may or may not be customized by different users. Multiple series enable higher degree of flexibility in satisfying different users' individual needs.

In another embodiment, additional workflow stages, such as Calcium Score (which is quantification of the amount of calcified atherosclerotic plaque in a patient coronary or other arteries) or Left Ventricular Ejection Fraction (EF, which is quantification of the fraction of the blood contained in the left ventricle (main pumping chamber) of the heart at its most distended that is ejected with each pumping cycle) Score, are defined in the Workflow Template 310. A first workflow stage relating to the selection of the centerline through a vessel (which is the definition of a curved line in 3D space that approximates the center of the vessel's lumen along its course) may also be included in the Workflow Template 310. A second workflow stage to display a curved reformat (a projection view where the path of the vessel in 3D is represented in a single 2D view) of the vessel to allow the diameter of the vessel to be measured and compared may be defined in the Workflow Template 310 as a dependent upon the first workflow stage.

In one embodiment, take one series of Workflow Scene 320 in FIG. 3 as an example, even though Stage 321 and Stage 322 of the Workflow Scene 320 have been performed, a technologist or physician may re-evaluate or re-process Stage 321 by applying Scene 327 to the medical image data. The application of Scene 327 recreates the workflow processing to the state it was when Scene 327 was last saved. As such, the user is provided with greater flexibility in fine-tuning or re-processing Stage 321. After completion, metadata generated from the fine-tuning or re-processing may be saved again to Scene 327. Since Stage 322 depends on State 321, the modification of Scene 327 will be reflected in the medical image views generated by applying Scene 328 to medical image data.

Figure 4:
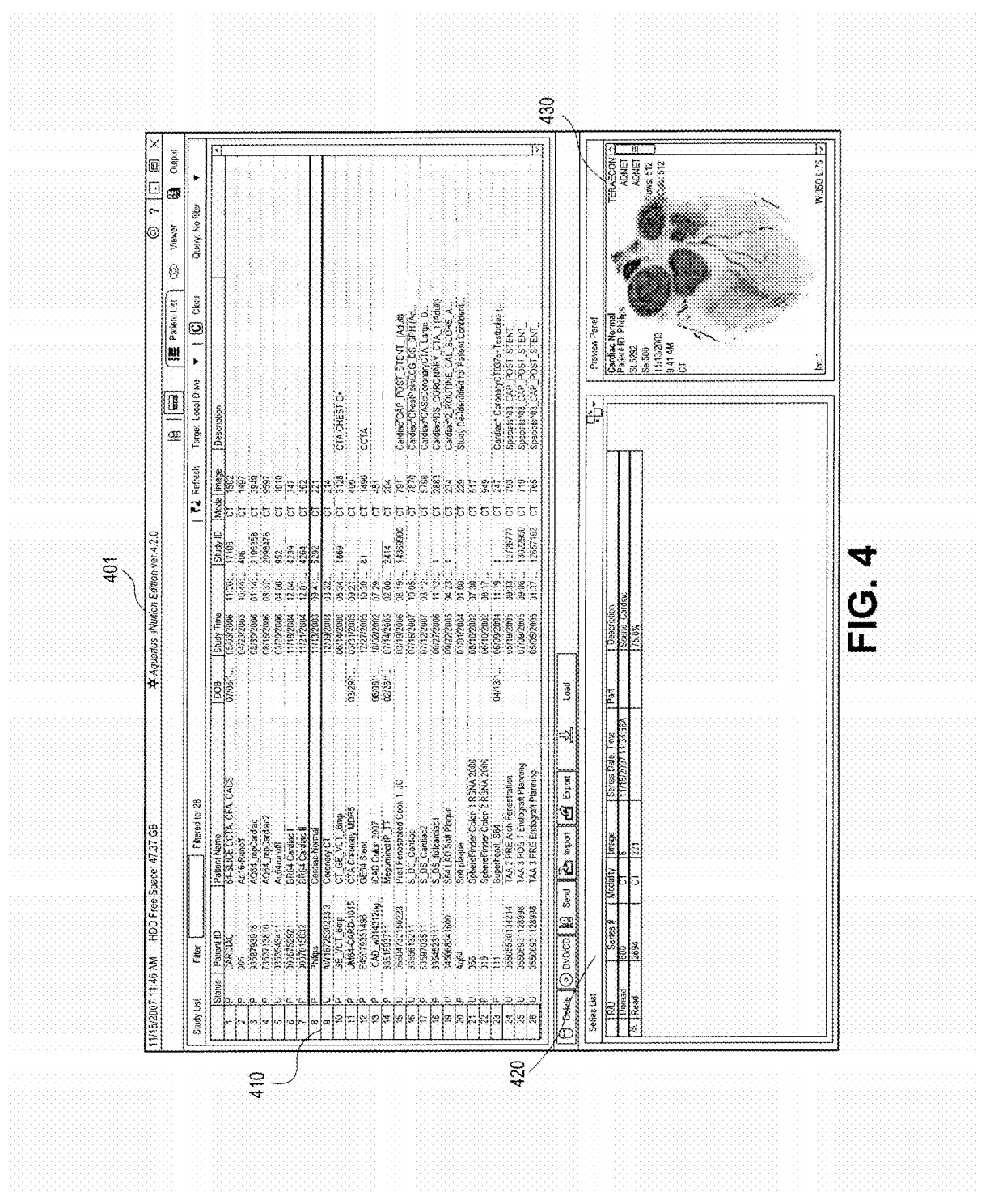

FIG. 4 illustrates an exemplary User Interface 401 of the Workflow Management System, in accordance with one embodiment of the present invention. User Interface 401 includes three viewing panels 410-430. Panel 410 illustrates a list view of studies that are managed by the Workflow Management System. Each study in the Panel 410 includes information such as, name and ID of the patient, the study ID and number of images stored within the study, etc. The patient ID and study ID are associated with DICOM objects stored and managed by Workflow Management Server 140 of FIG. 1. For example, when a user selects study 8, as illustrated in FIG. 4, related DICOM objects for the workflow scenes are retrieved using the patient ID and study ID, and displayed in Panels 420 and 430.

In one embodiment as illustrated in Panel 420, two series are listed with respect to the particular study. The second series, which stores the original medical image data collected by a CT modality, contains 221 slices of images. The first series is a workflow scene previously created by applying a workflow template to medical image data stored in the second series. As indicated in FIG. 4, the metadata stored in the first workflow scene may be used to generate 5 medical image views. When the first series is selected, Panel 430 shows a preview of the workflow scene. In one embodiment, the preview panel provides a medical image view generated from the latest generated scene of the workflow scene.

Figure 5:
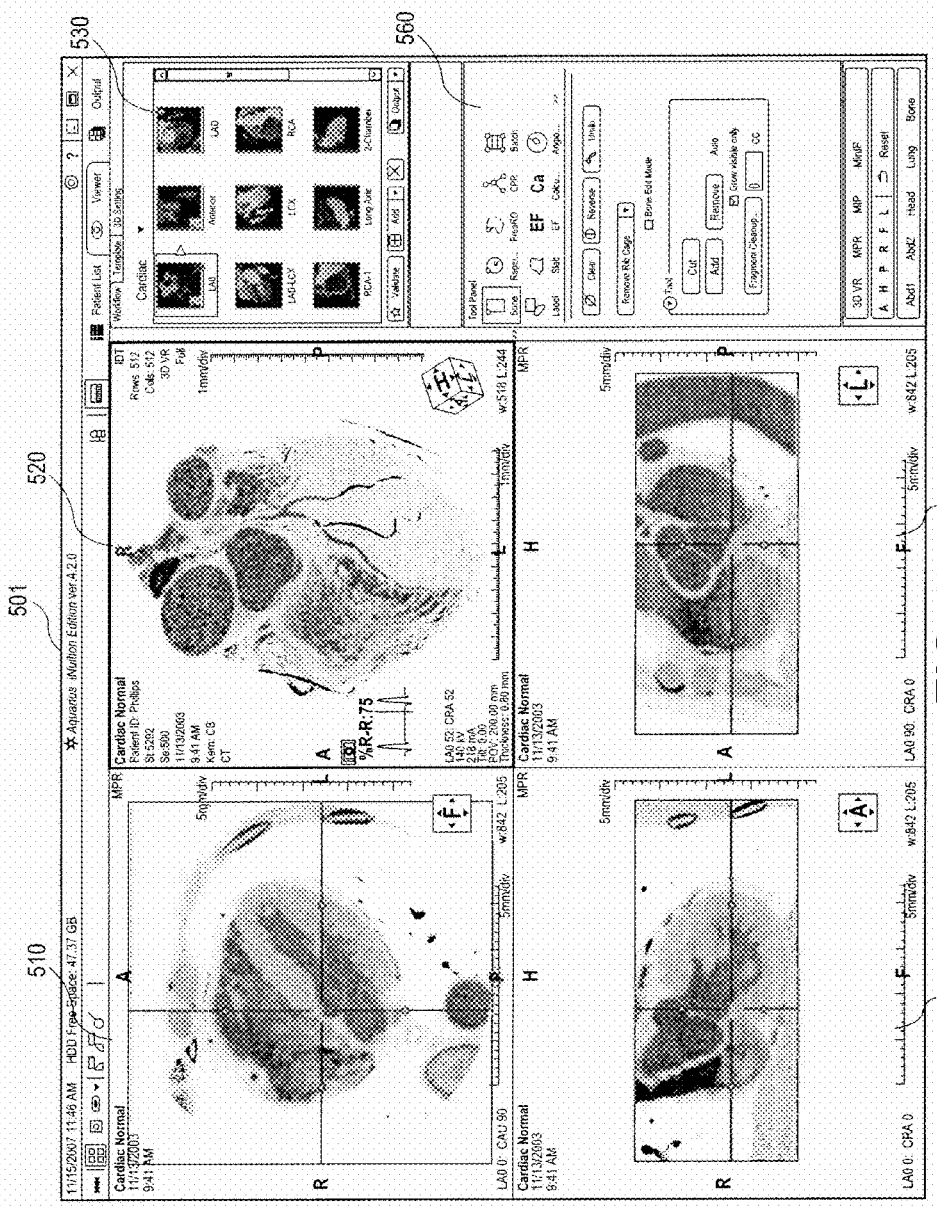
FIG. 5 illustrates another exemplary Workflow Management System user interface, in accordance with one embodiment of the present invention.

FIG. 5 illustrates an exemplary User Interface 501 showing a workflow template being applied to a study, in accordance with one embodiment of the present invention. The User Interface 501 includes Panels 510-560.

In one embodiment, Panel 530 illustrates a workflow scene with 12 workflow stages visible. The order of these 12 workflow stages is arranged in a left to right, top to down fashion. For example, as illustrated in FIG. 5, a workflow stage, Left Anterior Oblique (LAO), is applied to a patient's medical image data. The icon for LAO is shown with a thickened border, indicating it being the current processing workflow stage. Stage LAO generates metadata for rendering multiple views of the patient's heart, and Panels 510, 520, 540 and 550 are the resulted medical image views of above generated metadata. In one embodiment, once finishes reviewing the medical image views in Panels 510, 520, 540 and 550, a user could validate the workflow stage LAO by click on a "Validate" button. The validation action creates a scene to save the above generated metadata, associates the created scene with the workflow stage LAO, and stores the scene into the workflow scene. Afterwards, the icon for LAO stage has a "V" appearing near the right bottom, indicating that the result medical image views in Panels 510, 20, 540 and 550 are accepted by the user.

In another embodiment as illustrated in FIG. 5, after one workflow stage is validated, the Workflow Management System automatically proceeds to the next stage of the workflow, "Anterior," and awaits user command for processing. Alternatively, the Workflow Management System searches from the Medical Data Storage 160 of FIG. 1 for any automatically generated scene for this specific stage. If a scene that is previously generated by the Advanced Preprocessing Server 150 of FIG. 1 is found, the metadata stored in the scene would be quickly applied to the medical image data to produce the medical image views. This approach is advantageous because it incorporates automated preprocessing into workflow processing, thereby saving time and resource.

Referring back to FIG. 5, in one embodiment, Panel 520 shows a 3D rendered view of a patient's heart with ribcage removed. Panel 510 shows a view of the heart from the direction of the feet (an "Axial Slice" view). Panel 540 shows an anterior view of the heart (a "Coronal Slice" view). Panel 550 shows a left view of the heart (a "Sagittal Slice" view). All images in these four panels are user adjustable. In another embodiment, Panel 560 displays a set of tools available for processing and manipulation of the medical image views displayed in Panels 510, 520, 540 and 550. The set of tools are customized for each specific workflow stage, and for each specific medical image views. By using the tools provided in Panel 560, a user is not restricted by the predefined workflow stages in processing the image data. Further, any manual adjustments to the medical image views are recorded and saved into the workflow scene once the user completes the adjustments and validates the workflow stage. In another embodiment, a user may customize the workflow by adding additional workflow stages into an existing workflow scene. The processing of adding additional workflow stages is similar to the adding workflow stages in creating a workflow template, as described below.

Figure 6A:
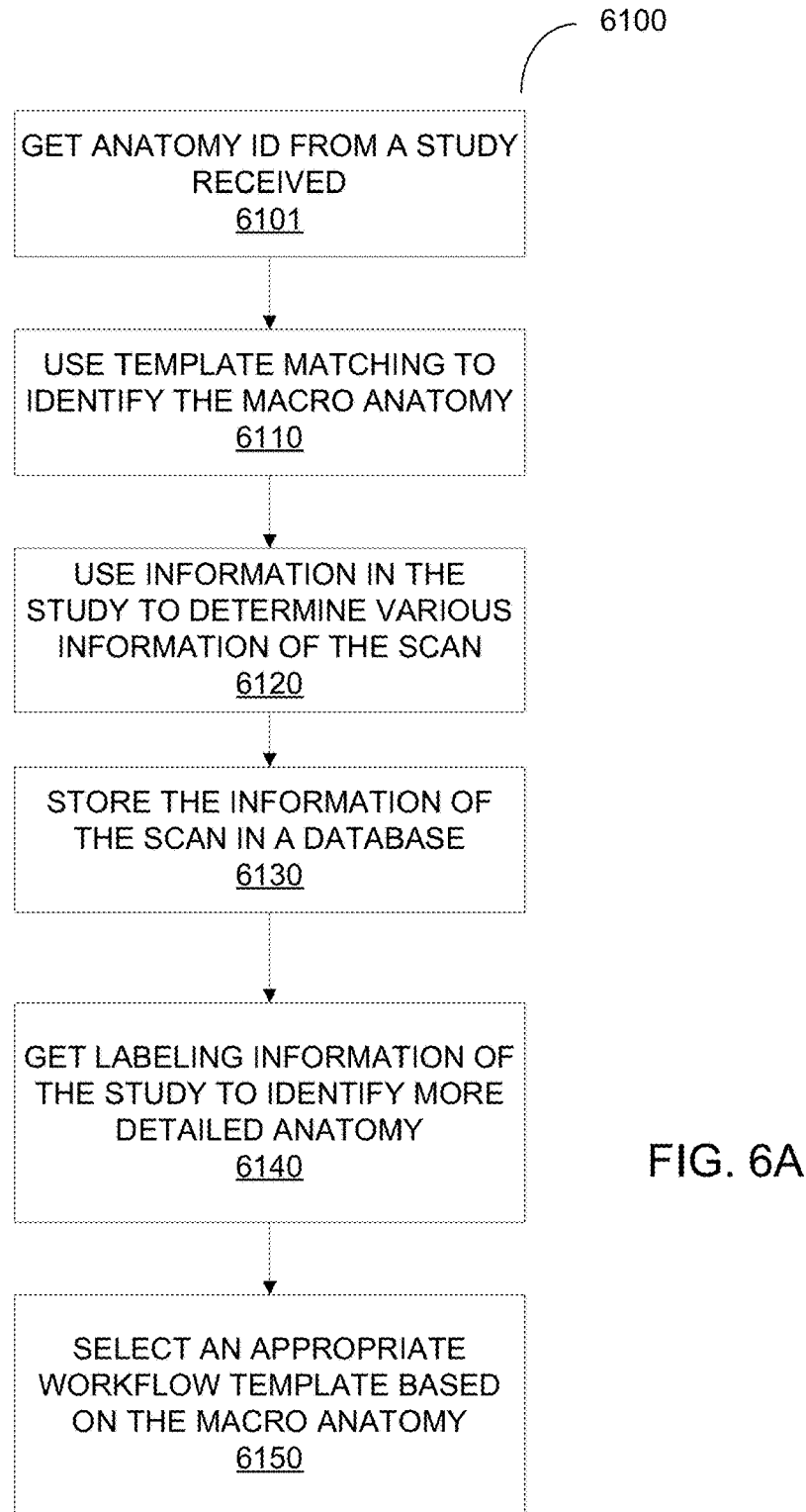
FIG. 6A illustrates a flow diagram of a method to automatically select a predefined workflow template according to one embodiment of the present invention.

FIG. 6A illustrates a flow diagram of a method 6100 to automatically select a predefined workflow template according to one embodiment of the present invention. The method 6100 may be performed by processing logic that may comprise hardware (e.g., circuitry, dedicated logic, programmable logic, microcode, etc.), software (such as instructions run on a processing device), or a combination thereof. For example, a Workflow Management System running on a Workflow Management Server 140 of FIG. 1 may perform all or part of the method 6100.

Initially, processing logic gets anatomy identification (ID) from a study received at block 6101. The study may include data or results of one or more scans from various medical imaging devices discussed above. The study may be received via push or an import from media (e.g., importing from a computer readable medium, such as a compact disc, or from a file electronically transmitted to the Workflow Management System, etc.). At block 6110, processing logic uses template matching to identify the macro anatomy of the study. In general, a macro anatomy broadly refers to a major body part, such as the head, the heart, the chest, etc.

At block 6120, processing logic uses information in the study to determine various information of the scan. For instance, processing logic may use sorting information to identify if the scan in the study is four-dimensional (4D). Alternatively, processing logic may use the R-R information to identify if the scan is a cardiac scan. In some embodiments, processing logic uses the dimensions of the scan to determine if it is a RUNOFF scan. At block 6130, the information of the scan determined is stored in a database (such as Medical Data Storage 160 in FIG. 1). At block 6140, processing logic may get labeling information of the study to identify more detailed anatomy of the scan.

Finally, at block 6150, processing logic automatically selects an appropriate workflow template based on the macro anatomy. For example, processing logic may launch a predefined cardiac workflow template if the scan is determined to be a cardiac scan. Likewise, processing logic may launch a predefined site runoff workflow template if the scan is determined to be a RUNOFF scan. In some embodiments, As such, processing logic provides a default workflow template for each type of scan. In some embodiments, processing logic further allows users to customize the default templates to be launched for each individual user. For instance, processing logic may associate an identification of an individual user (e.g., a user name) and a certain type of scan with a particular workflow template the individual user has selected (which may be referred to as a user-specific default workflow template or a customized default workflow template). Then processing logic automatically launches the user-specific default workflow template when the user receives a study including data of the certain type of scan.

Figure 6B:
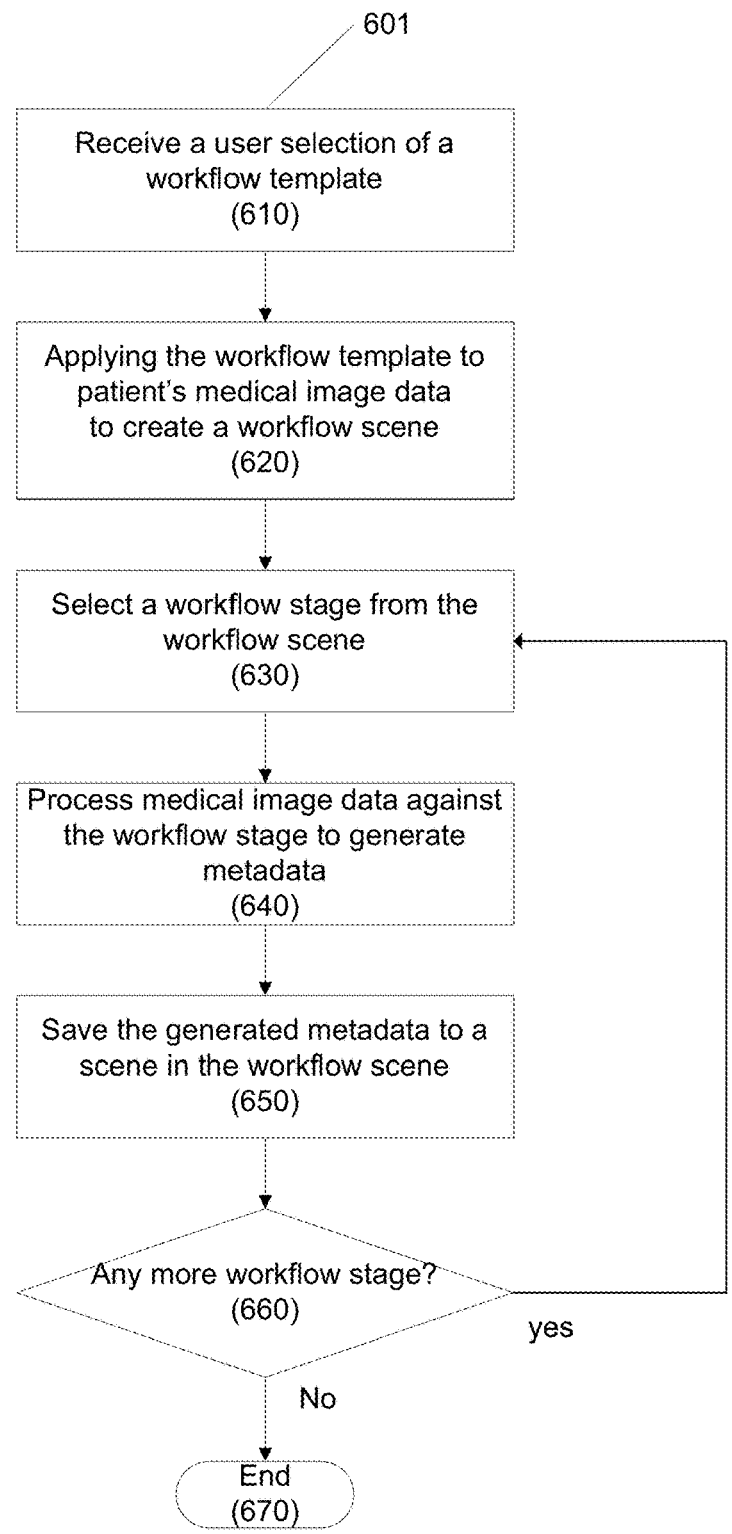
FIG. 6B illustrates a flow diagram of a method for applying a workflow template to a set of medical image data in accordance with one embodiment of the present invention.

FIG. 6B illustrates a flow diagram of a Method 601 for applying a predefined workflow template to a set of medical image data, in accordance with one embodiment of the present invention. The Method 601 may be performed by processing logic that may comprise hardware (e.g., circuitry, dedicated logic, programmable logic, microcode, etc.), software (such as instructions run on a processing device), or a combination thereof. In one embodiment, Method 601 is performed by a Workflow Management System running on a Workflow Management Server 140 of FIG. 1.

Referring back to FIG. 6B, in one embodiment, at Block 610, to process a particular medical study, the Workflow Management System receives a user selection of one of the predefined workflow templates to be applied to a patient's medical image data. Alternatively, the Workflow Management System may automatically select a predefined workflow template as described above with reference to FIG. 6A. At Block 620, the Workflow Management System applies the selected workflow template to the patient's medical image data, and creates a workflow scene based on the selected workflow template. The workflow scene, which may be used to save all the metadata generated during the workflow processing, contains the workflow stages predefined in the selected workflow template. At Block 630, the Workflow Management System receives a user selection of a workflow stage to be performed next. At Block 640, the image processing operations defined in the workflow stage are applied to the medical image data. The application of the workflow stage generates metadata and multiple medical image views. The medical image views are rendered based on one or more image processing parameters in the metadata.

In one embodiment, at Block 650, after a user is satisfied with the medical image views generated by the metadata from the selected workflow stage, along with any additional customization that has been done by the user, the user validates the workflow stage. Once validated, a new scene is created. The above metadata is saved to the scene. The scene is associated with the workflow stage, and stored to the collection of scenes in the workflow scene. In one embodiment, the medical image views are not saved. Rather, the metadata for generating the medical image views from the medical image data is saved. This approach requires less storage, while providing high level of flexibility.

At Block 660, a determination is made as to whether the next stage of the workflow template should be applied. In one embodiment, once a user has validated a scene, the Workflow Management System automatically selects the next stage on the workflow sequence for processing. If there are more workflow stages, the Method 601 proceeds to block 630. Otherwise, the method proceeds to the end Block 680.

Figure 7:
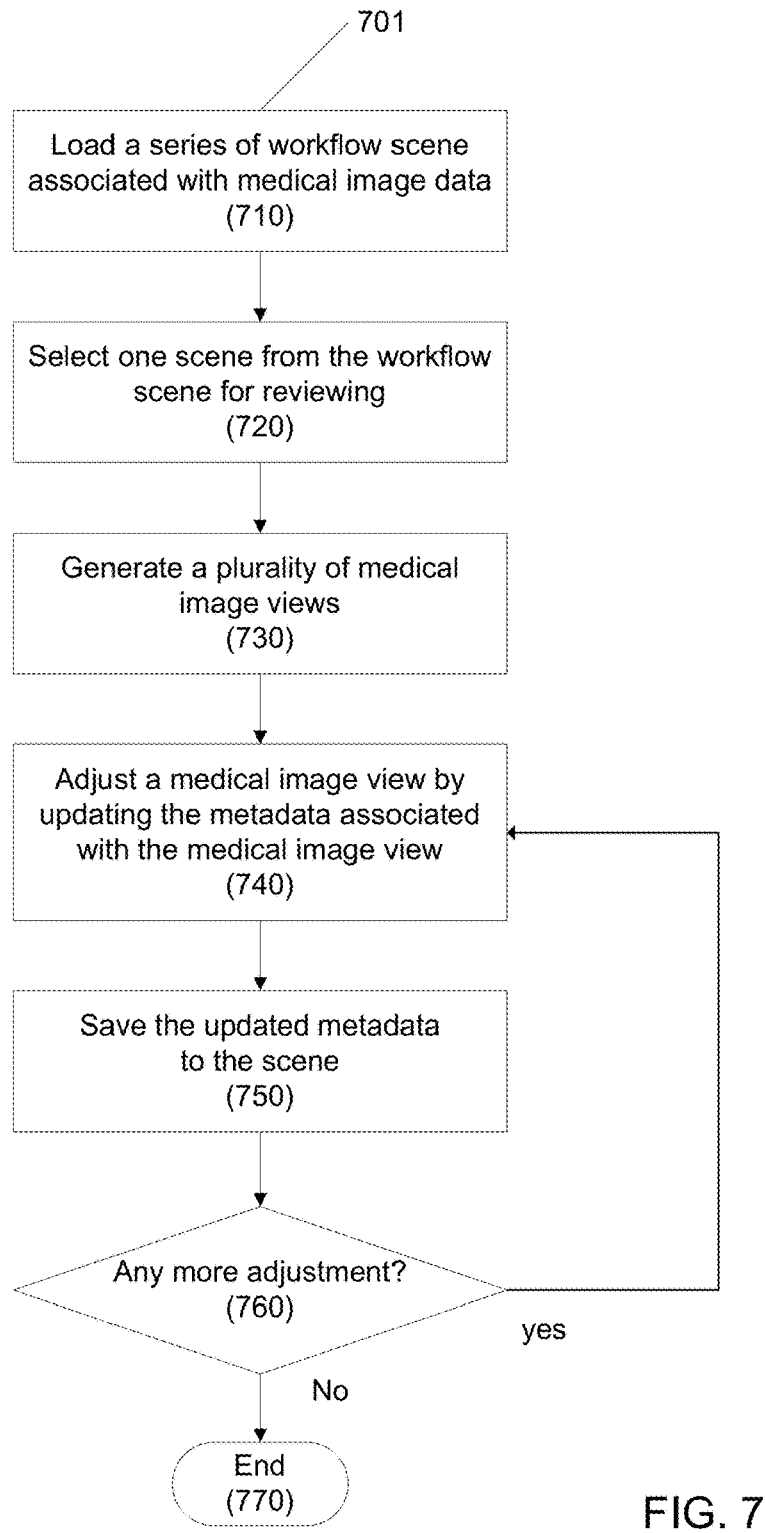
FIG. 7 illustrates a flow diagram of a method for modifying an existing workflow scene, in accordance with one embodiment of the present invention.

FIG. 7 illustrates a flow diagram of a Method 701 for reviewing a workflow scene, in accordance with one embodiment of the present invention. The Method 701 may be performed by processing logic that may comprise hardware, software, or a combination thereof. In one embodiment, Method 701 is performed by Workflow Management System running on the Workflow Management Server 140 of FIG. 1.

Referring back to FIG. 7, in one embodiment, at Block 710, a series of a workflow scene is loaded by the Workflow Management System, and applied to the medical image data associated with the workflow scene. At Block 720, one previously created scene is selected from the loaded workflow scene for reviewing, and is applied to the medical image data associated with the workflow scene. At Block 730, multiple medical image views are generated after the application of the image processing parameters stored in the selected scene. The rendered multiple medical image views may appear substantially the same as the end results previously generated during the creation of the select scene. At Block 740, the Workflow Management System receives user requests to adjust one of the medical image views. The adjustments are made by making updates to the image processing parameters stored in the selected scene. In one embodiment, the Workflow Management System provides a customized set of tools specifically tailored to adjustments of the metadata stored in the selected scene. At Block 750, once the user is satisfied with the adjusted medical image views, the Workflow Management System saves the updated metadata associated with the adjustment as a replacement scene back to the workflow scene. Later, when another user selects the updated replacement scene for reviewing, the adjusted medical image views are reproduced. In another embodiment, the new metadata does not replace the original metadata in the workflow scene. Instead, the new metadata may be stored in a second series of workflow scene, allowing a user to review both series of workflow scenes.

At Block 760, a determination is made as to whether the Workflow Management System receives any more user adjustment. If additional user requests are received, Method 701 proceeds to Block 740. Otherwise, Method 701 proceeds to end Block 770.

Figure 8:
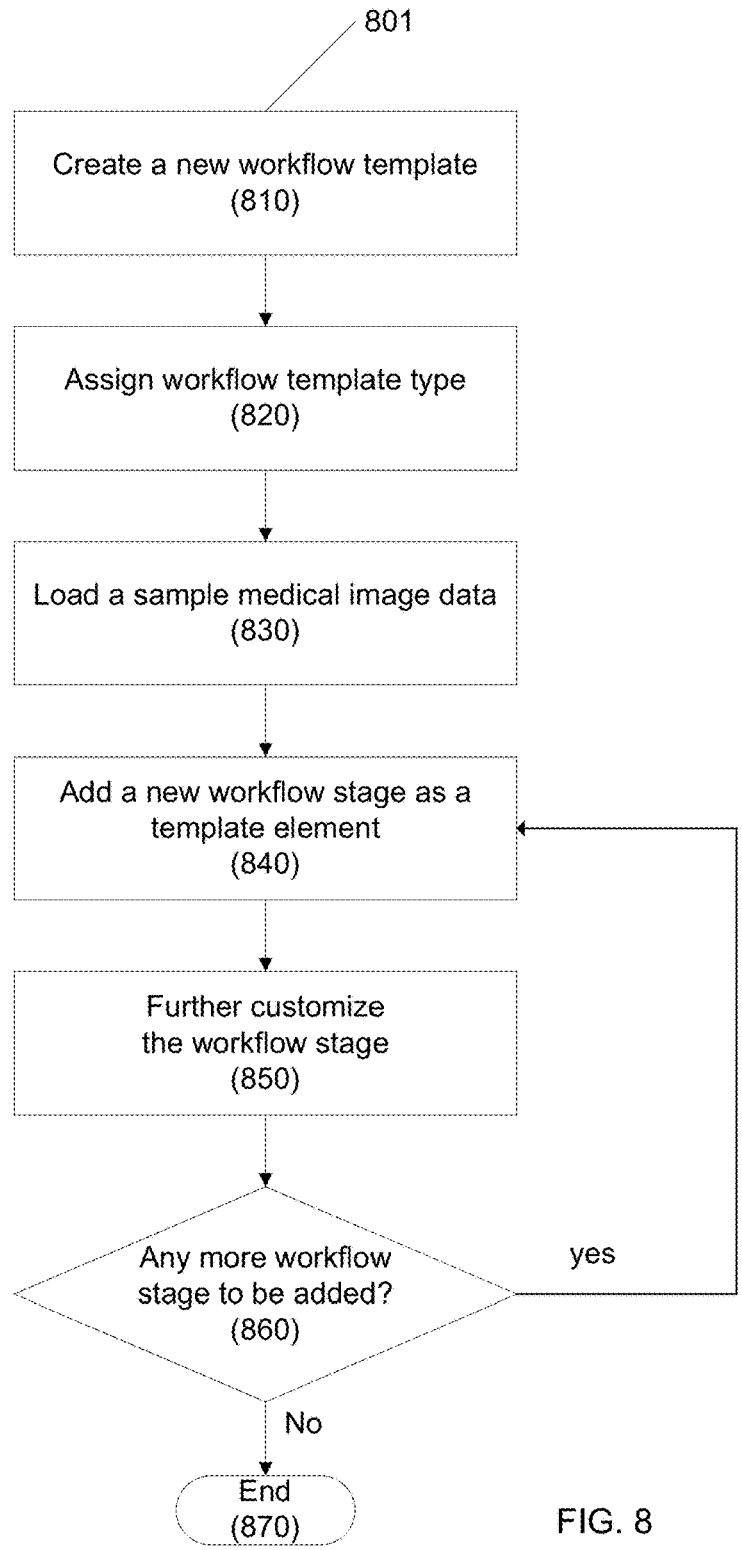
FIG. 8 illustrates a flow diagram of a method for creating a new workflow template, in accordance with one embodiment of the present invention.

FIG. 8 illustrates a flow diagram of a Method 801 for creating a new workflow template that can be applied to medical image data, in accordance with one embodiment of the present invention. The Method 801 may be performed by processing logic that may comprise hardware, software, or a combination thereof. In one embodiment, Method 801 is performed by the Workflow Management Server 140 of FIG. 1. In a further embodiment, Method 801 may be initiated by a user request received from a 3D workstation 120 or a 3D Thin Client 110 of FIG. 1.

Referring back to FIG. 8, in one embodiment, at Block 810, a user request is received to create a new workflow template. The user who has initiated the create request may provide a name for the new workflow template as well as any optional comments along with the request. At Block 820, a second user request is received to assign a template type to the newly created template. A template type, such as an organ, (e.g., heart), or a body part, (e.g., head), provides Workflow Management System a starting point in performing image processing. Further, the template type allows workflow elements to customize their image processing operations based on the specific characteristics of the body parts.

In one embodiment, at Block 830, a sample set of medical image data is loaded to provide previewing and customization of workflow template. At Block 840, a new workflow stage is added into the workflow template. The new workflow stage is selected from a list of pre-defined workflow stages that are related to the type of the workflow template. For example, when adding a new workflow stage called "bone removal," if the system recognizes that the template type is for cardiac analysis of a heart, then the new workflow stage may be set up to perform a more specific "ribcage removal." At Block 850, a user may perform additional customization of the added new workflow stage. The customization may be performed on the loaded sample set of medical image data to record image processing in addition to the operations provided by the pre-defined image processing operations of the workflow stage. The customized image processing operations are generated when a user manipulates and adjusts the medical image views via a set of tools provided. Once completed, the customizations may be recorded and saved into the workflow stage, which is stored in the new workflow template. Later, when applying this workflow template to a new set of medical image data in creating a workflow scene, the customized operations would be performed as recorded to the new set of medical image data. In one embodiment, Block 850 may be optional if the operations provided by the pre-defined workflow stage are satisfactory.

At Block 860, a determination is made as to whether there are any more workflow stages to be added. If there are more workflow stages to be added, Method 801 proceeds to Block 840. Alternatively, Block 860 proceeds to Block 870 and terminates by saving the newly created workflow template along with the added workflow stages to the Workflow Management System. The newly created workflow template is available for usage.

In the above description, numerous details are set forth. It will be apparent, however, to one skilled in the art, that various embodiments of the present invention may be practiced without these specific details. In some instances, well-known structures and devices are shown in block diagram form, rather than in detail, in order to avoid obscuring the present invention.

Some portions of the detailed description which follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "determining", "calculating", "filtering", "displaying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A data storage device may include a machine-accessible storage medium (also known as a machine-readable storage medium) on which is stored on or more sets of instructions (e,g, software) embodying any one or more of the methodologies or functions described herein. The software may also reside, completely or at least partially, within a main memory and/or within a processing device during execution thereof by a computer system, the main memory and the processing device also constituting machine-accessible storage media. The software may further be transmitted or received over a network via a network interface device.

The term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instructions for execution by the machine and that cause the machine to perform any one or more of the methodologies of the present invention. The term "machine-accessible storage medium" shall accordingly be taken to include, but not be limited to, solid-state memories, optical and magnetic media, etc.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A computer-implemented method for processing medical images, the method comprising:
    storing a plurality of workflow templates, each including a predefined sequence of workflow stages associated with a particular type of medical diagnosis or process, wherein each workflow stage defines one or more image processing operations to be performed including one or more inputs required and one or more outputs to be produced, and wherein at least one workflow stage generates metadata specifying one or more image processing parameters to be used as an input by another workflow stage for processing a corresponding medical image;
    in response to a request from a user to process a medical image data, automatically determining a user identifier (ID) that identifies the user based on the request;
    identifying, based on the user ID, at least one of the workflow templates that is specifically configured to process the medical image data associated with the user;
    pre-processing the medical image data including performing on the received medical image data one or more image processing operations automatically based on a plurality of workflow stages of the identified workflow template that is independent of a specific imaging device that generated the medical image data to generate at least a scene automatically corresponding to a workflow stage of the plurality of workflow stages, and wherein the at least one scene shows an image view representing the medical image data; and
    storing the at least one scene corresponding to a workflow stage in a persistent storage by storing only metadata associated with the at least one automatically generated scene without storing the associated image views, wherein the at least one scene includes metadata used to recreate a corresponding medical image view subsequently, wherein the metadata includes one or more image processing parameters corresponding to one or more image processing operations performed on the received medical image data to automatically generate the at least one scene, wherein the automatically generated at least one scene provides a history of operations performed in the workflow stage while workflow stages without any associated scenes show all the remaining operations yet to be performed.

2. The method of claim 1, wherein the at least one workflow template was configured as a default workflow template for the user.

3. The method of claim 1, wherein identifying at least one of the workflow templates based on the user ID comprises:
    identifying a set of one or more workflow templates that is associated with the user ID;
    determining a type of the medical image data based on the medical image data; and
    selecting from the set of workflow templates the at least one workflow template that is associated with the type of the medical image data.

4. The method of claim 3, wherein the at least one workflow template was created by the user prior to receiving the request to process the medical image data, including specifying the at least one workflow template is associated with the type of the medical image data.

5. The method of claim 1, wherein the scenes associated with the workflow stages of the workflow template are collectively stored as part of a workflow scene, and wherein the workflow scene is used to track all image processes that have been performed for a first workflow defined by the workflow template.

6. The method of claim 5, wherein the workflow scene can be used to identify which of the workflow stages have been processed and which of the workflow stages have not been processed.

7. The method of claim 1, wherein the workflow stages of the workflow template are sequentially performed according to an order defined by the workflow template.

8. The method of claim 1, wherein an operation performed on a second workflow stage includes at least one of zooming, viewing projections, removing data from a first image view represented by a first workflow stage, and wherein the second workflow stage generates metadata representing a second image view that is different from the first image view.

9. The method of claim 1, further comprising:
    in response to a selection of the scene representing a first workflow stage of the workflow template, presenting a set of image processing tools via a user interface, wherein the set of image processing tools are specifically tailored to metadata associated with the scene;
    in response to a selection of a first of the image processing tools, adjusting the image view represented by the scene using the first image processing tool; and updating metadata of the first workflow stage of the workflow template based on the adjustment of the image view of the first workflow stage.

10. The method of claim 9, further comprising storing the updated workflow template as a second workflow template separated from the workflow template.

11. The method of claim 1, wherein at least one of the workflow templates includes a workflow stage that depends on multiple workflow stages, wherein a predefined sequence of workflow stages is associated with a particular type of medical diagnosis or process, and wherein each workflow stage defines one or more image processing operations to be performed.

12. The method of claim 1, wherein at least one of the workflow templates includes multiple workflow stages that depend on a single workflow stage, wherein a predefined sequence of workflow stages is associated with a particular type of medical diagnosis or process, and wherein each workflow stage defines one or more image processing operations to be performed.

13. A non-transitory machine-readable medium having instructions stored therein, which when executed by a processor, cause the processor to perform operations for processing medical images, the operations comprising:
storing a plurality of workflow templates, each including a predefined sequence of workflow stages associated with a particular type of medical diagnosis or process, wherein each workflow stage defines one or more image processing operations to be performed including one or more inputs required and one or more outputs to be produced, and wherein at least one workflow stage generates metadata specifying one or more image processing parameters to be used as an input by another workflow stage for processing a corresponding medical image;
in response to a request from a user to process a medical image data, automatically determining a user identifier (ID) that identifies the user based on the request;
identifying, based on the user ID, at least one of the workflow templates that is specifically configured to process the medical image data associated with the user;
pre-processing the medical image data including performing on the received medical image data one or more image processing operations automatically based on a plurality of workflow stages of the identified workflow template that is independent of a specific imaging device that generated the medical image data to generate at least a scene automatically corresponding to a workflow stage of the plurality of workflow stages, and wherein the at least one scene shows an image view representing the medical image data; and
storing the at least one scene corresponding to a workflow stage in a persistent storage by storing only metadata associated with the at least one automatically generated scene without storing the associated image views, wherein the at least one scene includes metadata used to recreate a corresponding medical image view subsequently, wherein the metadata includes one or more image processing parameters corresponding to one or more image processing operations performed on the received medical image data to automatically generate the at least one scene, wherein the automatically generated at least one scene provides a history of operations performed in the workflow stage while workflow stages without any associated scenes show all the remaining operations yet to be performed.

14. The non-transitory machine-readable medium of claim 13, wherein the at least one workflow template was configured as a default workflow template for the user.

15. The non-transitory machine-readable medium of claim 13, wherein
identifying at least one of the workflow templates based on the user ID comprises:
identifying a set of one or more workflow templates that is associated with the user ID;
determining a type of the medical image data based on the medical image data; and
selecting from the set of workflow templates the at least one workflow template that is associated with the type of the medical image data.

16. The non-transitory machine-readable medium of claim 15, wherein the at least one workflow template was created by the user prior to receiving the request to process the medical image data, including specifying the at least one workflow template is associated with the type of the medical image data.

17. The non-transitory machine-readable medium of claim 13, wherein the scenes associated with the workflow stages of the workflow template are collectively stored as part of a workflow scene, and wherein the workflow scene is used to track all image processes that have been performed for a first workflow defined by the workflow template.

18. The non-transitory machine-readable medium of claim 17, wherein the workflow scene can be used to identify which of the workflow stages have been processed and which of the workflow stages have not been processed.

19. The non-transitory machine-readable medium of claim 13, wherein the workflow stages of the workflow template are sequentially performed according to an order defined by the workflow template.

20. The non-transitory machine-readable medium of claim 13, wherein an operation performed on a second workflow stage includes at least one of zooming, viewing projections, removing data from a first image view represented by a first workflow stage, and wherein the second workflow stage generates metadata representing a second image view that is different from the first image view.

21. A data processing system, comprising:
a processor; and
memory coupled to the processor for storing instructions therein, which when executed from the memory, cause the processor to perform operations, the operations including storing a plurality of workflow templates, each including a predefined sequence of workflow stages associated with a particular type of medical diagnosis or process, wherein each workflow stage defines one or more image processing operations to be performed including one or more inputs required and one or more outputs to be produced, and wherein at least one workflow stage generates metadata specifying one or more image processing parameters to be used as an input by another workflow stage for processing a corresponding medical image,
in response to a request from a user to process a medical image data, automatically determining a user identifier (ID) that identifies the user based on the request,
identifying, based on the user ID, at least one of the workflow templates that is specifically configured to process the medical image data associated with the user, pre-processing the medical image data including performing on the received medical image data one or more image processing operations automatically based on a plurality of workflow stages of the identified workflow template that is independent of a specific imaging device that generated the medical image data to generate a scene automatically corresponding to a workflow stage of the plurality of workflow stages, and wherein the at least one scene shows an image view representing the medical image data, and storing the at least one scene corresponding to a workflow stage in a persistent storage by storing only metadata associated with the at least one automatically generated scene without storing the associated image views, wherein the at least one scene includes metadata used to recreate a corresponding medical image view subsequently, wherein the metadata includes one or more image processing parameters corresponding to one or more image processing operations performed on the received medical image data to automatically generate the at least one scene, wherein the automatically generated at least one scene provides a history of operations performed in the workflow stage while workflow stages without any associated scenes show all the remaining operations yet to be performed.

22. The system of claim 21, wherein the at least one workflow template was configured as a default workflow template for the user.

23. The system of claim 21, wherein identifying at least one of the workflow templates based on the user ID comprises:
  identifying a set of one or more workflow templates that is associated with the user ID;
  determining a type of the medical image data based on the medical image data; and
  selecting from the set of workflow templates the at least one workflow template that is associated with the type of the medical image data.

24. The system of claim 23, wherein the at least one workflow template was created by the user prior to receiving the request to process the medical image data, including specifying the at least one workflow template is associated with the type of the medical image data.

* * * * *